(12) United States Patent
Galen et al.

(10) Patent No.: US 9,113,830 B2
(45) Date of Patent: Aug. 25, 2015

(54) SYSTEMS AND METHODS FOR DETECTING AND MONITORING ARRHYTHMIAS USING THE PPG

(75) Inventors: Peter Galen, Portland, OR (US); Paul Addison, Edinburgh (GB); James Watson, Dunfermline (GB); Scott McGonigle, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 375 days.

(21) Appl. No.: 13/118,995

(22) Filed: May 31, 2011

(65) Prior Publication Data

US 2012/0310100 A1 Dec. 6, 2012

(51) Int. Cl.
*A61B 5/02* (2006.01)
*A61B 5/1455* (2006.01)
*A61B 5/00* (2006.01)

(52) U.S. Cl.
CPC ............ *A61B 5/14551* (2013.01); *A61B 5/726* (2013.01); *A61B 5/7282* (2013.01)

(58) Field of Classification Search
USPC .......................... 600/324, 481, 483, 485, 500
See application file for complete search history.

(56) References Cited

U.S. PATENT DOCUMENTS

| | | | |
|---|---|---|---|
| 4,289,141 A | 9/1981 | Cormier | |
| 5,439,483 A | 8/1995 | Duong-Van | |
| 5,590,650 A | 1/1997 | Genova | |
| 5,632,272 A | 5/1997 | Diab et al. | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |

(Continued)

FOREIGN PATENT DOCUMENTS

| | | |
|---|---|---|
| EP | 0841034 A1 | 5/1998 |
| JP | 09-084776 A | 3/1997 |

(Continued)

OTHER PUBLICATIONS

Addison, Paul S., The Illustrated Wavelet Transform Handbook, Taylor & Francis Group, 2002, pp. 1-353.

(Continued)

*Primary Examiner* — Etsub Berhanu
(74) *Attorney, Agent, or Firm* — Shvarts & Leiz LLP

(57) ABSTRACT

Systems and methods for detecting and monitoring arrhythmias from a signal are provided. A signal processing system may transform a signal using a wavelet transformation and analyze changes in features of the transformed signal to detect pulse rhythm abnormalities. For example, the system may detect pulse rhythm abnormalities by analyzing energy parameters, morphology changes, and pattern changes in the scalogram of a PPG signal. Further, the system may detect pulse rhythm abnormalities by analyzing both the PPG signal and its corresponding scalogram. Physiological information, such as cardiac arrhythmia, may be derived based on the detected pulse rhythm abnormality.

14 Claims, 14 Drawing Sheets

(56) References Cited

U.S. PATENT DOCUMENTS

| | | |
|---|---|---|
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,561,986 B2 | 5/2003 | Baura |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,931,269 B2 | 8/2005 | Terry |
| 6,993,377 B2 | 1/2006 | Flick |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,477,571 B2 | 1/2009 | Melese et al. |
| 7,515,949 B2 | 4/2009 | Norris |
| 7,519,488 B2 | 4/2009 | Fu |
| 7,523,011 B2 | 4/2009 | Akiyama et al. |
| 7,566,306 B2 | 7/2009 | Fujiwara et al. |
| 7,613,507 B2 | 11/2009 | Vitali et al. |
| 7,725,146 B2 | 5/2010 | Li et al. |
| 7,725,147 B2 | 5/2010 | Li et al. |
| 7,794,406 B2 | 9/2010 | Reisfeld et al. |
| 7,811,234 B2 | 10/2010 | McGrath |
| 7,819,812 B2 | 10/2010 | John et al. |
| 7,951,129 B2 | 5/2011 | Chinchoy |
| 8,478,389 B1* | 7/2013 | Brockway et al. ............ 600/509 |
| 2004/0230105 A1* | 11/2004 | Geva et al. ................... 600/301 |
| 2006/0211930 A1 | 9/2006 | Scharf et al. |
| 2006/0258921 A1 | 11/2006 | Addison et al. |
| 2007/0021673 A1 | 1/2007 | Arbel et al. |
| 2007/0106167 A1* | 5/2007 | Kinast ........................... 600/509 |
| 2007/0167694 A1 | 7/2007 | Causevic et al. |
| 2007/0282212 A1 | 12/2007 | Sierra et al. |
| 2008/0082018 A1 | 4/2008 | Sackner et al. |
| 2008/0214903 A1 | 9/2008 | Orbach |
| 2008/0243021 A1 | 10/2008 | Causevic et al. |
| 2009/0324034 A1 | 12/2009 | Watson et al. |
| 2009/0326353 A1* | 12/2009 | Watson et al. ................ 600/330 |
| 2009/0326395 A1 | 12/2009 | Watson et al. |
| 2010/0331715 A1* | 12/2010 | Addison et al. ............... 600/529 |
| 2011/0004069 A1* | 1/2011 | Ochs et al. ................... 600/300 |
| 2011/0071406 A1 | 3/2011 | Addison et al. |
| 2011/0074409 A1* | 3/2011 | Stoughton et al. ............ 324/307 |
| 2011/0301852 A1* | 12/2011 | Van Slyke ....................... 702/19 |

FOREIGN PATENT DOCUMENTS

| | | |
|---|---|---|
| WO | 0125802 A2 | 4/2001 |
| WO | 0162152 A1 | 8/2001 |
| WO | 03055395 A1 | 7/2003 |
| WO | 2004105601 A1 | 12/2004 |
| WO | 2005096170 | 10/2005 |
| WO | 2006085120 A1 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, vol. 21, No. 1, 2007, pp. 55-61.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, vol. 20, No. 1. 2006, pp. 33-36.

Leonard, Paul A., Clifton, David, Addison, Paul S., Watson, James N., Beattie, Tom "An Automated Algorithm For Determining Respiratory Rate By Photoplethysmogram In Children," Acta Paediatricia, 2006, 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Applicaiton," Journal of the Institute of Electronics, Information and Communication Engineers, vol. 76, No. 5, May 1993, pp. 518-528.

Andruschenko S. et al., "Extraction of the Diagnostic Parameters from the Pulse Plethysmogram During Real-Time Continuous Hemodynamic Monitoring," Biomedical Engineering, Conference: 1st Middle East Conference on Biomedical Engineering (MECBME), Feb. 21, 2011, pp. 256-259, IEEE.

Timm U. et al., "Optical Sensor System for Continuous Non-Invasive Hemodynamic Monitoring in Real-Time," Sensors Applications Symposium (SAS), Feb. 22, 2011, pp. 167-172, IEEE.

International Search Report for Application No. PCT/US2012/039946, mailed on Aug. 9, 2012.

* cited by examiner

SYSTEMS AND METHODS FOR DETECTING AND MONITORING ARRHYTHMIAS USING THE PPG

SUMMARY OF THE DISCLOSURE

The present disclosure relates to signal processing and, more particularly, the present disclosure relates to identifying heartbeat irregularities from a transformation of a photoplethysmograph (PPG) signal, for example from a wavelet transformation.

A pulse oximeter monitors oxygen saturation and heart rate. Current pulse oximeters are able to detect pulse rate and are therefore able to identify bradycardia (i.e., slow heart rates) and tachycardia (i.e., fast heart rates). However, current pulse oximeters are unable to identify other arrhythmia types (e.g., atrial fibrillation, ventricular fibrillation, ectopic beats, etc.).

The present disclosure describes systems and methods for detecting and monitoring arrhythmia by using a transformation (such as a wavelet transformation) of a received PPG signal. Detection of arrhythmia is important for several reasons. These include identifying potentially serious cardiovascular problems, identifying a change in the severity of existing problems, and keeping arrhythmias from interfering with physiological measurements. The disclosed methods and systems have particular use when an electrocardiograph (ECG) is not connected to a patient.

In some embodiments of the present disclosure, a method for determining cardiac arrhythmia in a subject may include receiving a PPG signal from a sensing device attached to a subject, generating a transformed signal based at least in part on a transformation of the PPG signal, and detecting a change in a feature of the transformed signal. The detected change may then be used to identify one or more pulse rhythm abnormalities, which may in turn be used to determine cardiac arrhythmia in the subject.

In some embodiments of the present disclosure, a system for determining cardiac arrhythmia in a subject may include a signal input and electronic processing equipment. The signal input may be configured to receive a PPG signal of a subject from a sensing device. The electronic processing equipment may be configured to receive the PPG signal and generate a scalogram based at least in part on a wavelet transformation of the photoplethysmograph signal. The electronic processing equipment may then determine an energy distribution of the scalogram for a time interval and compare it against a reference energy distribution to detect a change in the energy distribution of the pulse band region, the region of scales greater than the pulse band region, the region of scales lower than the pulse band region, any other suitable feature, or any combination thereof. In some embodiments, the detected change may be used to identify a pulse rhythm abnormality and determine cardiac arrhythmia in the subject.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
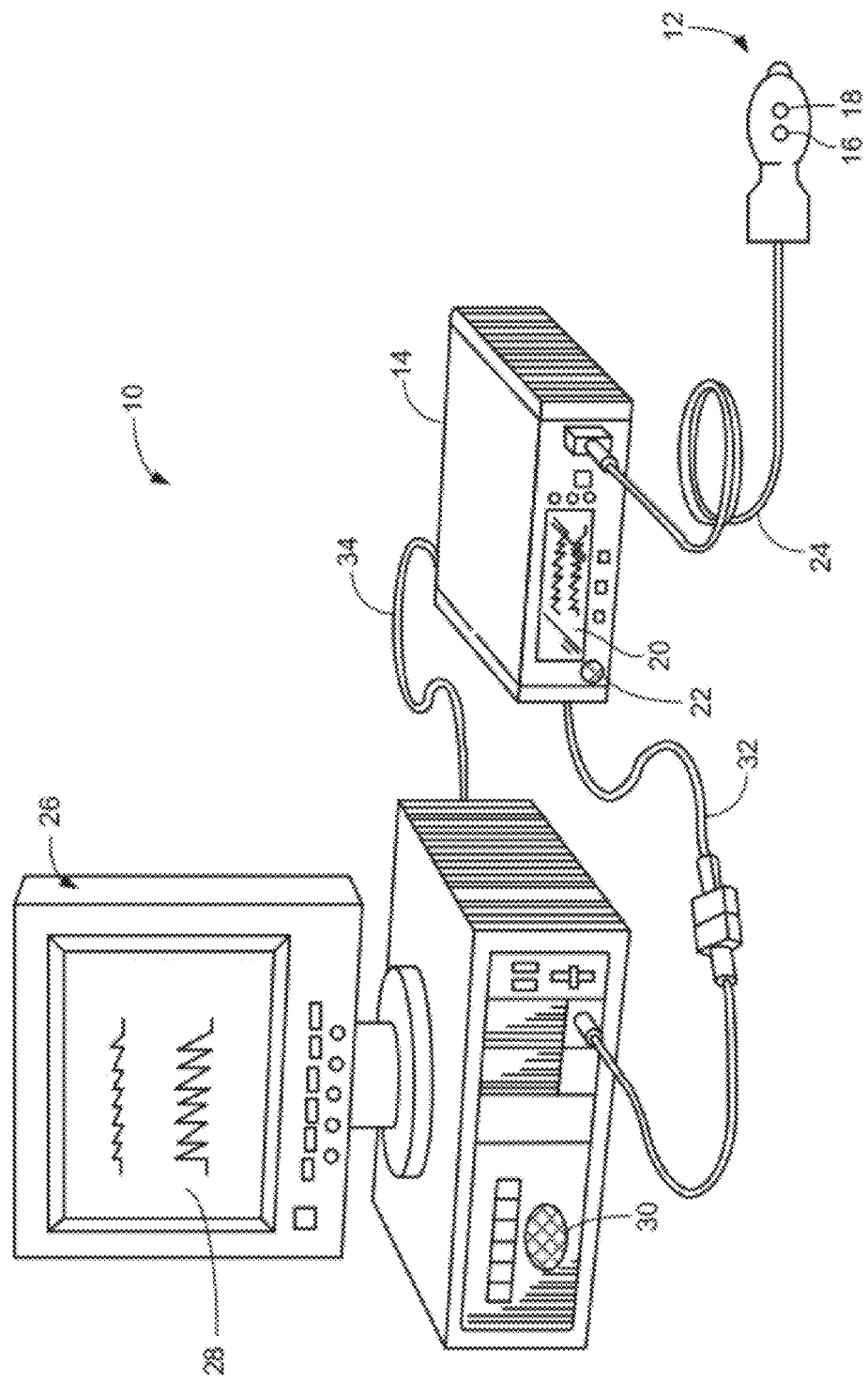
FIG. 1 shows an illustrative pulse oximetry system in accordance with an embodiment.

An oximeter is a medical device that is used to determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter passes light using a light source through blood perfused tissue and photoelectrically senses the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_O + (1-s)\beta_r)\frac{dl}{dt} \quad (3)$$

3. Red (3) is divided by IR (3)

$$\frac{\frac{d\log I(\lambda_R)}{dt}}{\frac{d\log I(\lambda_{IR})}{dt}} = \frac{s\beta_O(\lambda_R)+(1-s)\beta_r(\lambda_R)}{s\beta_O(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_O(\lambda_{IR}) - \beta_r(\lambda_{IR})) - \frac{d\log I(\lambda_{IR})}{dt}(\beta_O(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_O(\lambda_{IR}) - \beta_r(\lambda_{IR})) - \beta_O(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{\frac{dI}{dt}}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_r)-I(t_1,\lambda_R)]I(t_1,\lambda_{IR})$$

$$y(t)=Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to certain embodiments, system 10 includes a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
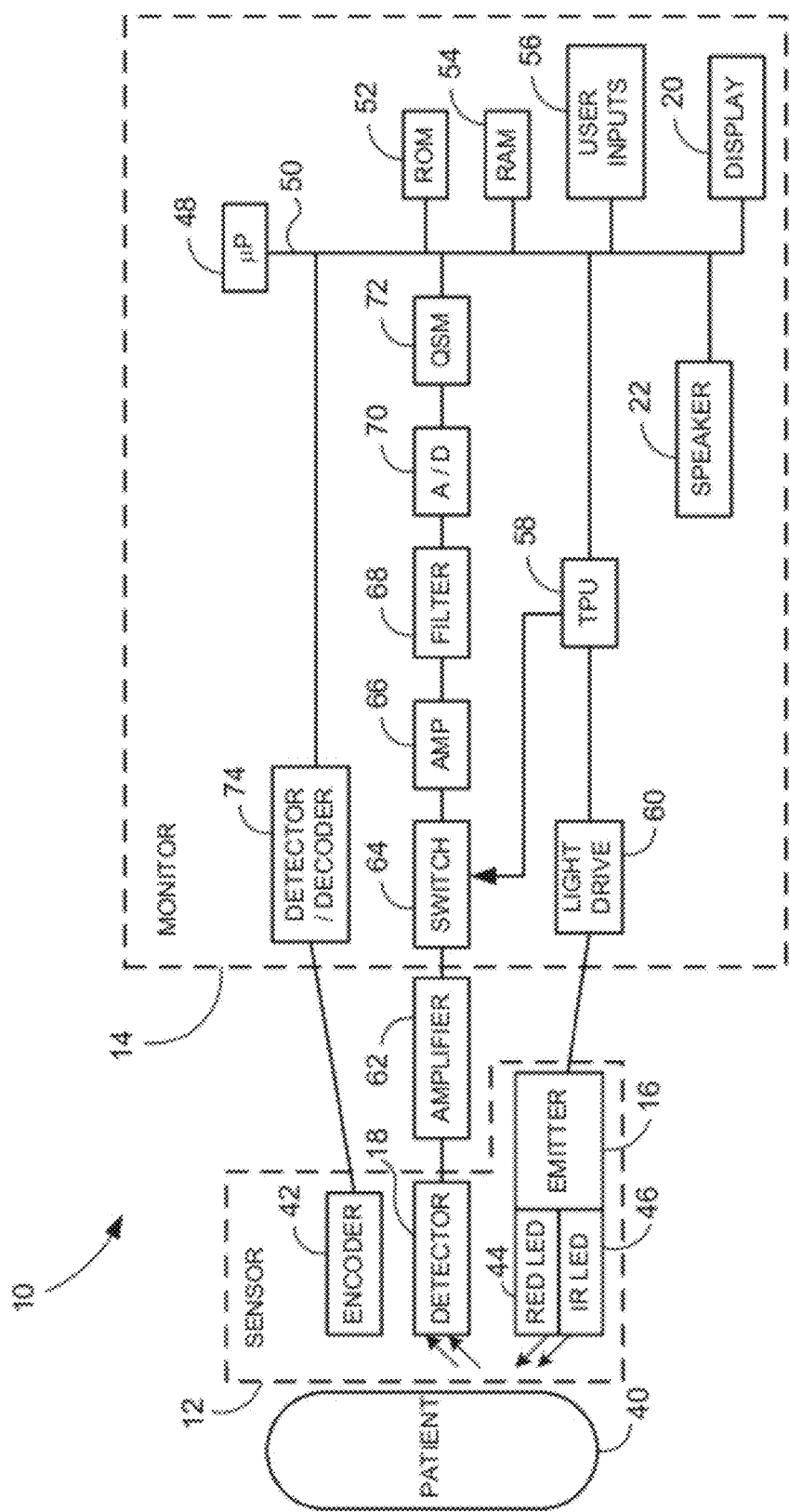
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In certain embodiments, a PPG signal is transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t) \psi * \left( \frac{t-b}{a} \right) dt \qquad (9)$$

where $\psi r*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '||' is the modulus operator. The scalogram may be rescaled for useful purposes. One common rescaling is defined as $$S_R(a,b) = \frac{|T(a,b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{j2\pi f_0 t}-e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
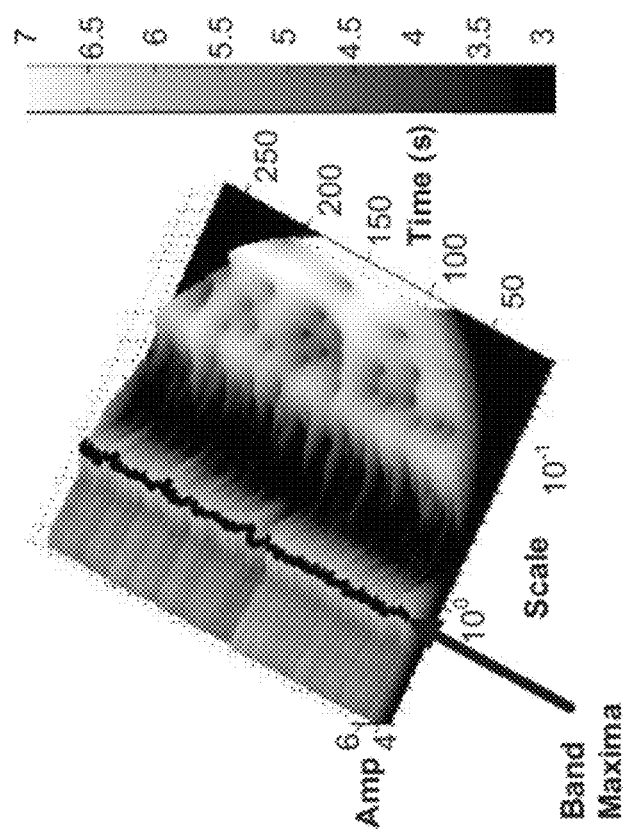
FIGS. 3(a) and 3(b) show illustrative views of a scalogram derived from a PPG signal in accordance with an embodiment.
Figure 3A:
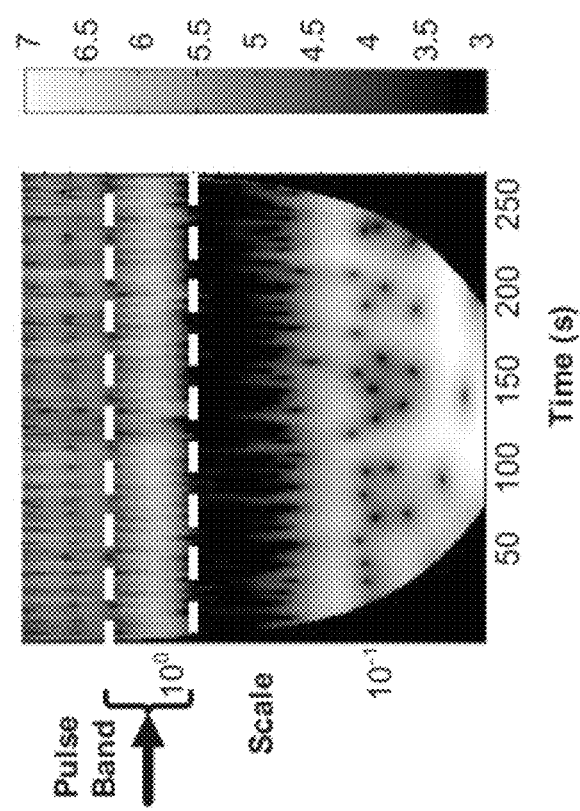

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heartbeat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
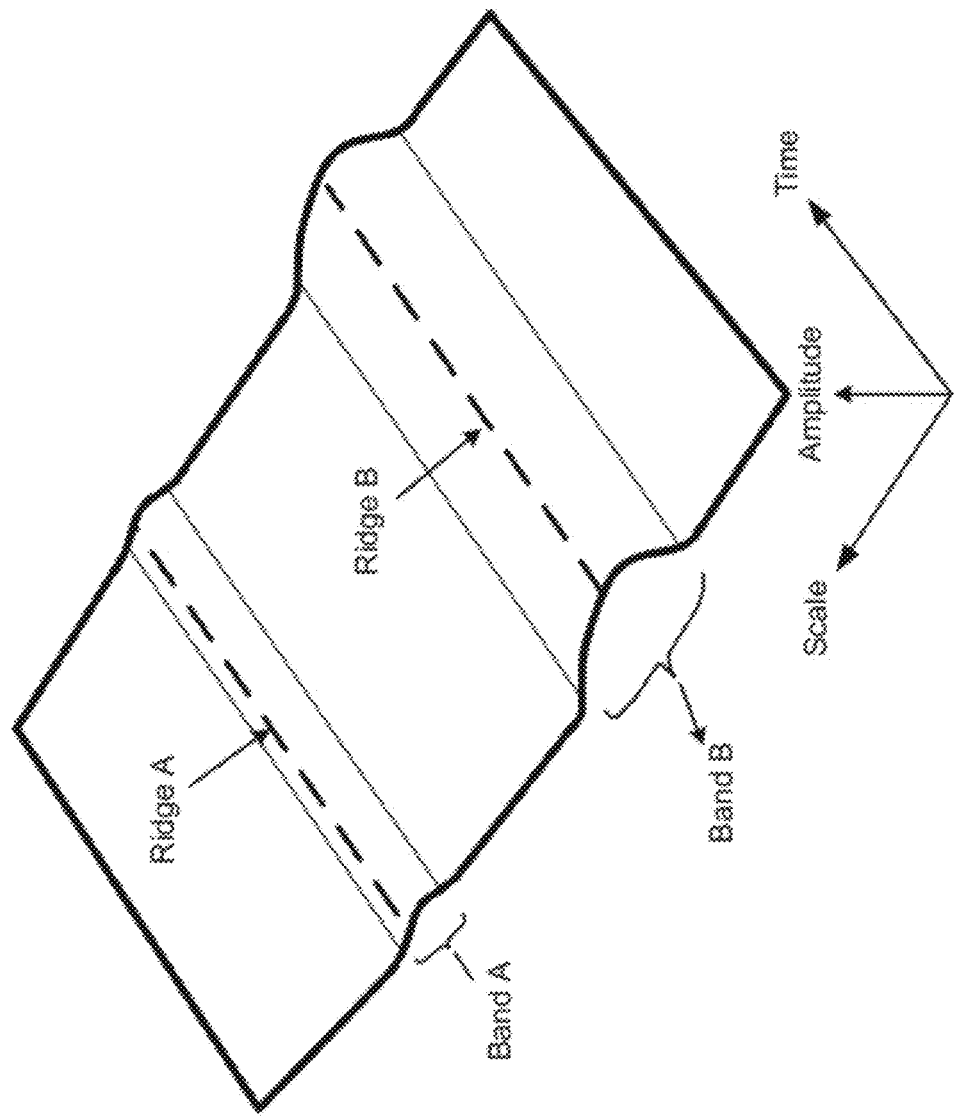
FIG. 3(c) shows an illustrative scalogram derived from a signal containing two pertinent components in accordance with an embodiment.
Figure 3D:
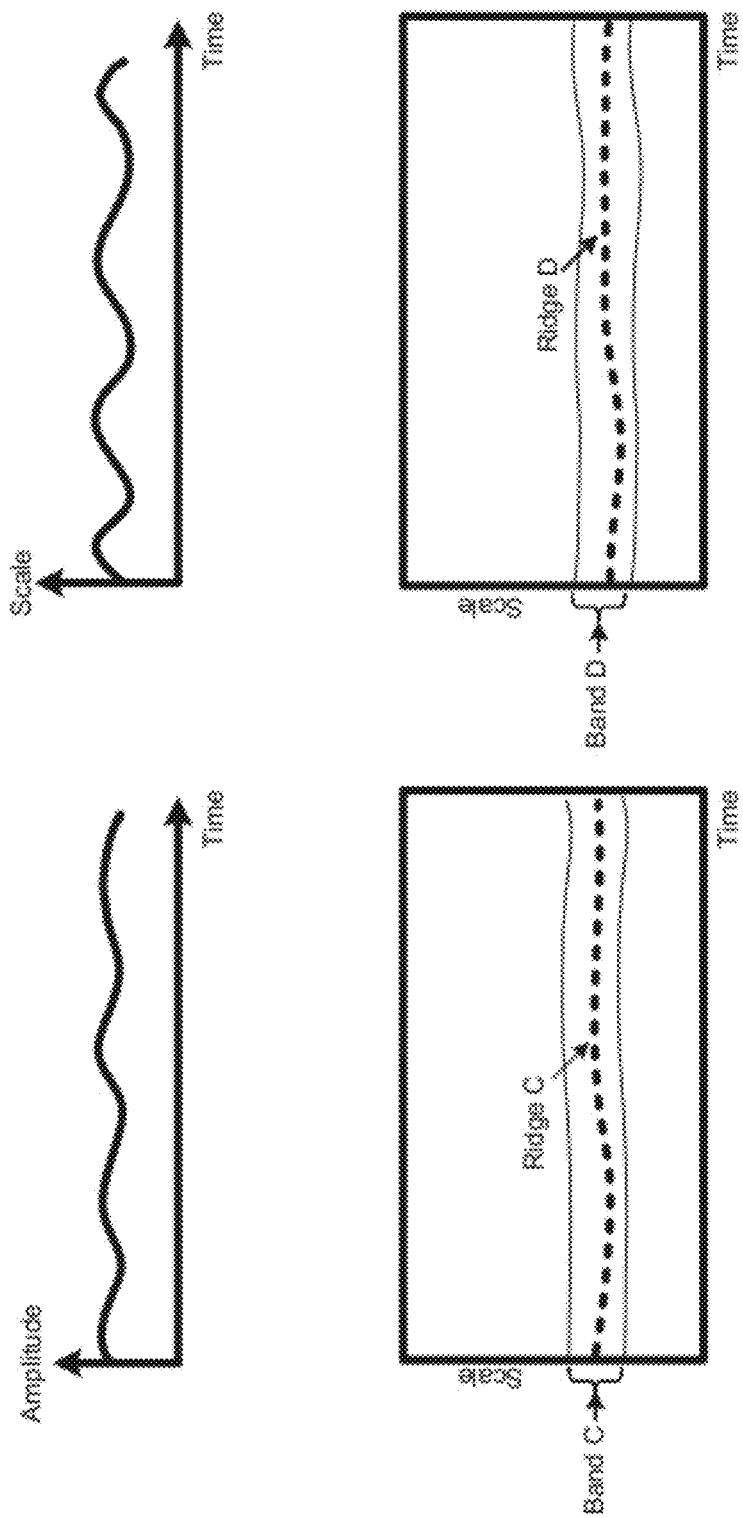
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\, db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\, db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
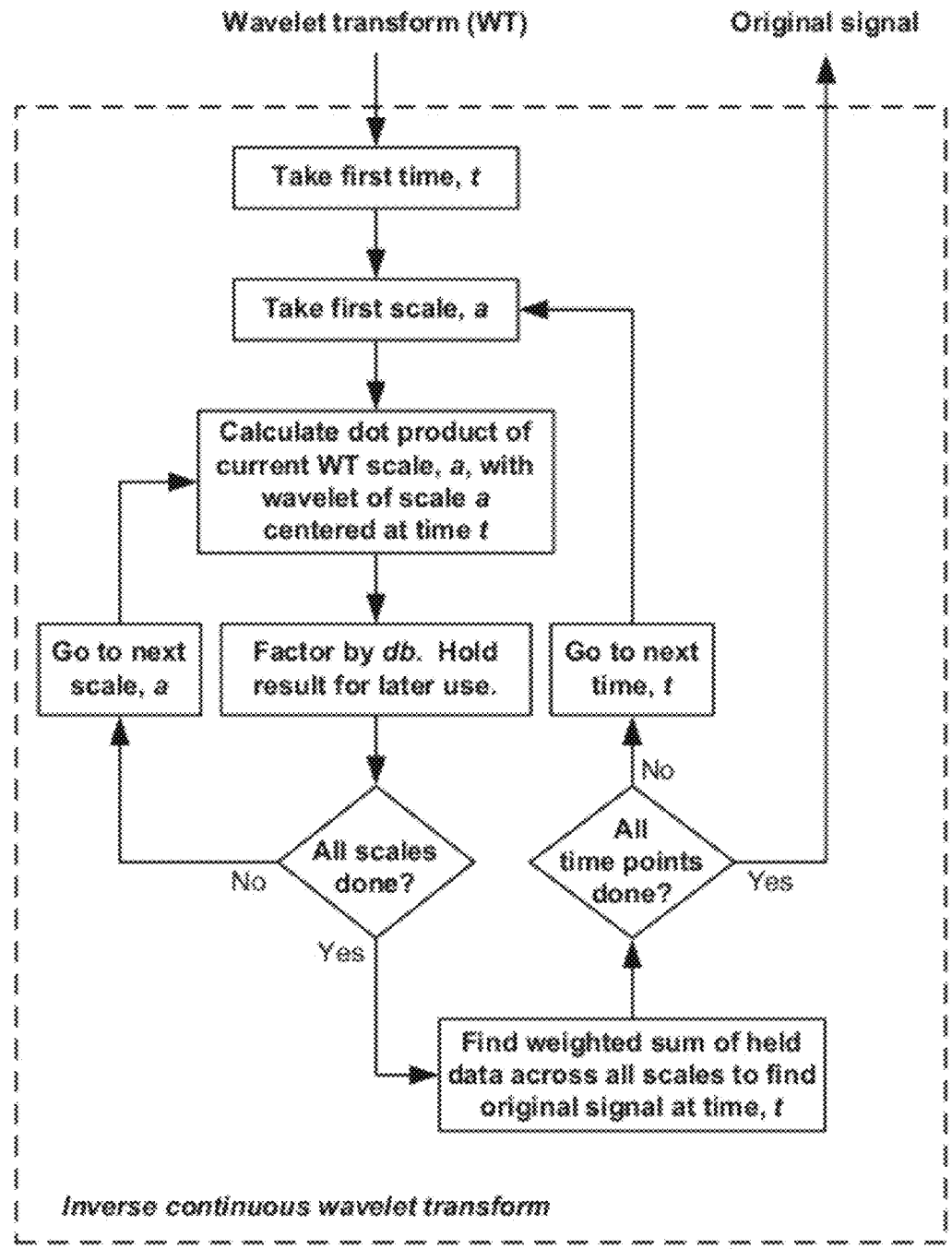
FIGS. 3(e) and 3(f) are flow charts of illustrative steps involved in performing an inverse continuous wavelet transform in accordance with embodiments.
Figure 3F:
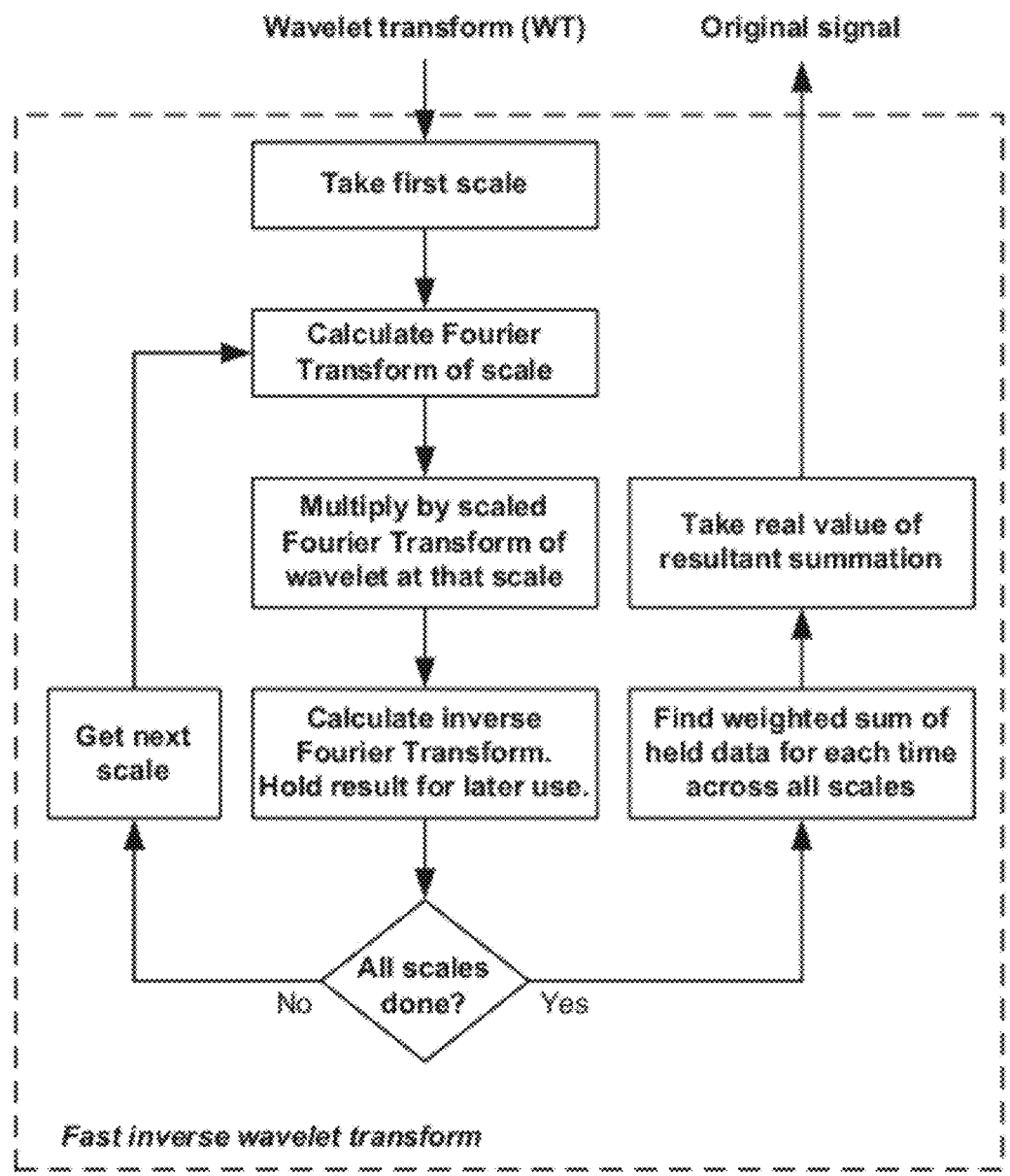

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
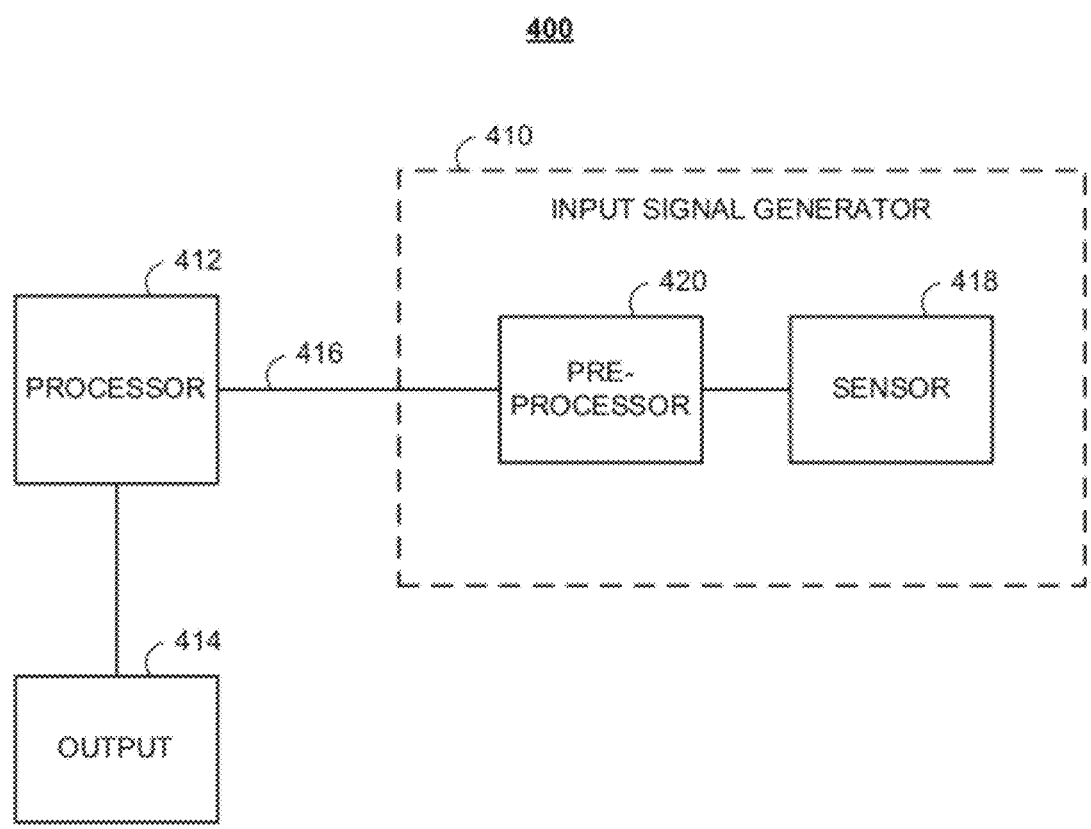
FIG. 4 is a block diagram of an illustrative continuous wavelet processing system in accordance with some embodiments.

FIG. 4 is an illustrative continuous wavelet processing system. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data, representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

The processing system may identify a change in a feature of the pulse rhythm of patient blood at the measurement site (e.g., the location on the patient's body associated with sensor 12). For example, the processing system may identify morphology changes, and corresponding pulse rhythm abnormalities may be detected in signals such as PPG signals. A pulse rhythm is the rhythmical throbbing of arteries produced by the regular contractions of the heart and may differ from a patient's heart rate, as a result of the patient's blood pressure, vasoconstriction, vasodilation, or other physiological attributes. With reference to the present context, a pulse rhythm abnormality may arise from an irregular firing of the heart that results in an identifiable morphology in the physiological signal, in a transformation of the signal such as a wavelet transformation, or both.

Figure 5:
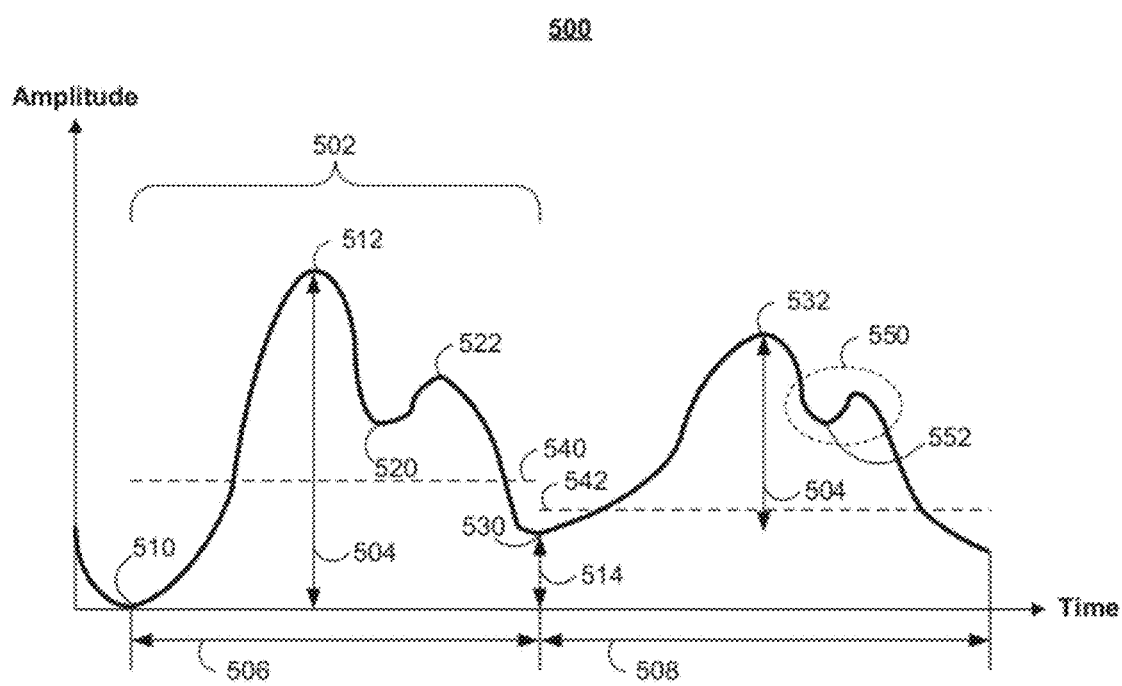
FIG. 5 shows signal characteristics of an illustrative PPG signal in accordance with some embodiments.

FIG. 5 shows PPG signal 500 that may be analyzed in accordance with the present disclosure. PPG signal 500 is an oscillating signal having pulses such as pulses 502. Each pulse of PPG signal 500 may correspond to a cardiac cycle. PPG signal 500 has AC component 504, which oscillates around baseline 540. For example, as shown in FIG. 5, during the time periods corresponding to different pulses or sets of pulses, PPG signal 500 may be oscillating around different baselines (e.g., baseline 540 during time period 506, baseline 542 during time period 508). The baseline of signal 500 may be calculated using any suitable technique. For example, the baseline may be calculated as an average of signal 500 over a selected amount of time or over a selected number of cardiac cycles.

In some embodiments, a signal processing system, such as signal processing system 400 of FIG. 4, receives PPG signal 500, and identifies one or more of local minimum point 510, local maximum point 512, local minimum point 520, and local maximum point 522 in the PPG signal 500. The signal processing system may pair each local minimum point with an adjacent maximum point. For example, the signal processing system may pair points 510 and 512 to identify one segment, points 512 and 520 to identify a second segment, points 520 and 522 to identify a third segment and points 522 and 530 to identify a fourth segment. The slope of each segment is measured to determine whether the segment corresponds to an upstroke portion of the pulse (e.g., a positive slope) or a downstroke portion of the pulse (e.g., a negative slope) portion of the pulse. A pulse may be defined as a combination of at least one upstroke and one downstroke. For example, the segment identified by points 510 and 512 and the segment identified by points 512 and 520 may define a pulse. In another example, the segments identified by points 510 and 530 may define a pulse.

In some embodiments, PPG signal 500 includes a dichrotic notch 550 or other notches (not shown) in different sections of the pulse (e.g., at the beginning (referred to as an ankle notch), in the middle (referred to as a dichrotic notch), or near the top (referred to as a shoulder notch). The signal processing system may identify notches and either utilize or ignore them when detecting the pulse locations. In some embodiments, the signal processing system computes the second derivative of the PPG signal to find the local minima and maxima points and uses this information to determine a location of, for example, a dichrotic notch. Additionally, the signal processing system may interpolate between points in signal 500 or between points in a processed signal using any interpolation technique (e.g., zero-order hold, linear interpolation, higher-order interpolation techniques). Some pulse detection techniques that may be performed by the signal processing system are described in more detail in co-pending, commonly assigned U.S. patent application Ser. No. 12/242,908, filed Sep. 30, 2008 and entitled "SYSTEMS AND METHODS FOR DETECTING PULSES IN A PPG SIGNAL," which is incorporated by reference herein in its entirety.

AC component 504 may be caused in part by a change in blood volume at a sensor location. The change in blood volume may be caused by the pressure wave generated by each heartbeat. The size of AC component 504 may correspond to the change in blood pressure at the sensor location (e.g., the difference between systolic and diastolic pressure in the arteries). As shown in FIG. 5, the amplitude of AC component 504 is higher during time period 506 than during time period 508. In addition to the AC component, PPG signal 500 also has amplitude component 514, which may be attributed to the total amount of absorption and/or transmission between the sensor emitter and detector. As shown in FIG. 5, amplitude component 514 also changes between time period 506 ("zero" amplitude) and time period 508.

In some embodiments, the signal processing system analyzes PPG signal 500 to calculate signal characteristics. The calculated signal characteristic may be any suitable characteristic such as an average or median amplitude of the AC component over a selected amount of time or over a selected number of cardiac events. For example, the signal processing system analyzes PPG signal 500 to calculate the length, amplitude, or both of a single downstroke portion of a pulse and an average value (e.g., mean, median) of the length, amplitude, or both of the downstroke portions of pulses over a selected amount of time or over a selected number of cardiac cycles. In other examples, the signal processing system analyzes PPG signal 500 to calculate the period of a single pulse and an average value (e.g., mean, median) of the period of pulses over a selected amount of time or over a selected number of cardiac cycles. In another example, the signal processing system may analyze PPG signal 500 to calculate the area of a single pulse and an average value (e.g., mean, median) of the area of pulses over a selected amount of time or over a selected number of cardiac cycles. It will be understood that the signal processing system may use any other suitable algorithm to calculate the desired signal characteristic.

The signal processing system may detect a pulse rhythm abnormality at a measurement site by calculating signal characteristics of PPG signal 500 and detecting changes in the signal morphology and characteristics. In some embodiments, the signal processing system characterizes one or more of the amplitude, timing, period, morphology, or other suitable characteristics of PPG signal 500 to detect a pulse rhythm abnormality. For example, the signal processing system may detect irregular pulses by comparing the length or the amplitude of a downstroke against a mean or median value. When the length of the amplitude of an individual downstroke exceeds a threshold value (e.g., 1.8 times the median value, or any other predetermined or calculated value), the downstroke may be identified as corresponding to an abnormal pulse. In another example, the signal processing system may detect abnormal pulses by comparing the period of a pulse against a mean or median value. When the period of an individual pulse exceeds a threshold value (e.g., 1.8 times the median value), the pulse may be identified as corresponding to an abnormal pulse. The signal processing system may also detect abnormal pulses by comparing the area of a pulse against a running mean or median value.

The signal processing system may monitor one or more signal characteristics to detect that a pulse rhythm abnormality has occurred. For example, as shown in FIG. 5, the length of a downstroke portion (e.g., from local maximum 512 to local minimum 520), the period of a pulse (e.g., the period corresponding to time period 506), or both may change to a different length (e.g., from local maximum 532 to local minimum 552), a different period (e.g., the period corresponding to time period 508), or both. The signal processing system may analyze these changes and determine that a pulse rhythm abnormality has occurred. For example, the signal processing system may detect that the patient has experienced an arrhythmia.

It will be understood that although a PPG signal as described above is suitable to detect events, other signals or devices may be used to detect events such as, for example, an electrocardiogram (ECG), electroencephalogram (EEG), electrogastrogram (EGG), electromyogram (EMG), heart rate signals, pathological sounds, ultrasound, or any other suitable biosignal, dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signals, or any combination thereof.

In some embodiments, the signal processing system may also detect an event by transforming a received signal. For example, the signal processing system may detect pulse rhythm abnormalities from within PPG signals by monitoring morphology changes in the PPG signal, analyzing a transformation of the PPG signal such as a wavelet transformation using a continuous wavelet transform, or using a combination of the signal and a transformed signal or signals. In some embodiments, the PPG signal may be differentiated before being processed, transformed, or both to better resolve the signal characteristics.

The detection of a pulse rhythm abnormality may be used to determine physiological information indicative of cardiac arrhythmia. For example, the signal processing system may identify or diagnose arrhythmias and heartbeat irregularities in the patient such as, for example, atrial flutter, atrial fibrillation, sinus tachycardia, ventricular tachycardia, ventricular fibrillation, bradycardia, bigeminy, trigeminy, an isolated irregularity such as an ectopic beat, any other suitable physiological information, or any combination thereof based on the pulse rhythm abnormality information. Illustrative pulse rhythm abnormalities are shown in FIGS. 6-9 in accordance with some embodiments of the present disclosure.

Figure 6:
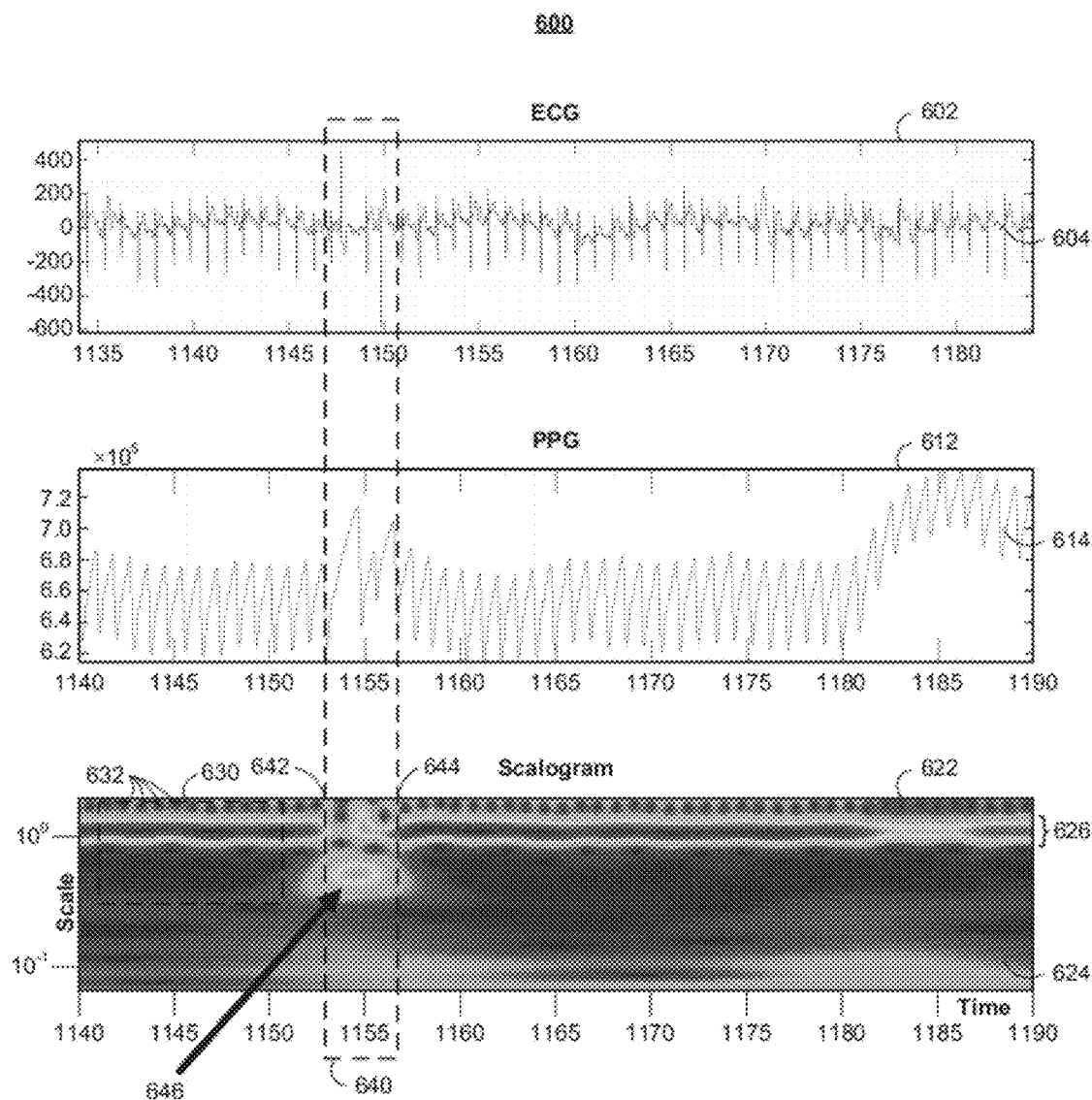
FIG. 6 shows an ECG signal, a PPG signal, and a corresponding scalogram of a PPG signal in accordance with some embodiments.

FIG. 6 illustrates a pulse rhythm abnormality in the form of an isolated irregularity, referred to as an ectopic. In particular, FIG. 6 shows amplitude-time plot 602 of an ECG signal 604, amplitude-time plot 612 of a PPG signal 614 taken at the same time as ECG signal 604, and scale-time-amplitude plot 622 of scalogram 624 generated from a continuous wavelet transform of PPG signal 614 in accordance with some embodiments. Scalogram 624 includes pulse band 626, calculation region 630, and isolated irregularity time period 640. Normal pulse rhythm occurs in the region before isolated irregularity time period 640 and resumes after isolated irregularity time period 640. Time is represented by the horizontal axes of plots 602, 612, and 622 while amplitude is represented by the vertical axes of plots 602 and 612 and the shading of plot 622 and scale is represented by the vertical axis of plot 622.

The signal processing system may use various metrics to detect the ectopic (and any other pulse rhythm abnormalities) within PPG signal 614, scalogram 624, or both. In some embodiments, the signal processing system characterizes the amplitude, timing, period, morphology, any other suitable characteristic, or any combination thereof of a pulse or pulses of PPG signal 614. In some embodiments, the signal processing system characterizes the morphology of localized energy increases below pulse band 626 and localized energy decreases on pulse band 626 of scalogram 624.

The signal processing system may calculate any suitable energy parameter within a region on the scalogram (e.g., region 630). The size and shape (e.g., horizontal and vertical ranges, aspect ratio) of region 630 may be selected in any suitable way. For example, the vertical range and location of region 630 may be selected to cover the pulse band 626. Pulse band 626 may vary its location and size over time. Therefore, in an embodiment, region 630 may be centered over the ridge of pulse band 626. The ridge of pulse band 626 may be identified, for example, using ridge following techniques or any other suitable technique such as using heart rate calculated from PPG signal 614. The ridge of the pulse band may be identified, for example, using the techniques described in Watson et al., U.S. patent application Ser. No. 12/245,326, filed Sep. 30, 2008, entitled "SYSTEMS AND METHODS FOR RIDGE SELECTION IN SCALOGRAMS OF SIGNALS," which is incorporated by reference herein in its entirety. With the ridge location known, the vertical range of region 630 may be selected to span a selected number of scales above and below the ridge. The number of scales may be selected such that region 630 spans only a portion of pulse band 626, all of pulse band 626, or all of pulse band 626 plus an additional amount. The vertical range and location of region 630 may be fixed to cover the range of scales where the pulse band is expected to be located based on historical heartbeat or pulse rhythm data for a certain patient or a certain patient type. For example, the vertical range of region 630 may span from a scale whose characteristic frequency is about 0.5 Hz to a scale whose characteristic frequency is about 4 Hz or equivalently 30-240 bpm. The horizontal range of region 630 may be selected to cover any suitable length of time, such as 1, 2, 3, 4, 5, etc. seconds. Region 630 may slide across the scalogram calculating the energy parameter in real-time or off-line. The energy parameter calculated within region 630 may be, for example, the average or median energy within the region.

The signal processing system may identify a morphology change and detect a pulse rhythm abnormality by comparing one or more parameters calculated within region 630 against an average value, such as a mean or median value, or any other suitable reference. In some embodiments, the signal processing system may identify a morphology change and detect a pulse rhythm abnormality when region 630, which may be progressing in time, reaches the region corresponding to region 640. For example, the signal processing system may detect a pattern of regular pulses 632. The signal processing system may detect a pulse rhythm abnormality in the form of isolated irregularity 646 (e.g., corresponding to an ectopic beat) by, for example, identifying a change in the pattern of regular pulses beginning at time 642, when the pattern of regular pulses ends, and ending at time 644, when the pattern of regular pulses resumes.

In the example of FIG. 6, the patient exhibits an isolated irregularity in region 640. Region 640 has a distinct morphology in scalogram 624 (as shown by the arrow pointing to region 646). The morphology of region 640 is distinct from normal because pulse band 626 breaks up and localized regions of higher energy 646 appear at lower scales (resulting in downshifting of energy to lower frequencies). The signal processing system may characterize the morphology change of localized energy increases below pulse band 626 and localized energy decreases on pulse band 626 and identify a pulse rhythm abnormality based on, for example, the morphology change. Thus, by analyzing particular morphology changes and characteristics in various regions of scalogram 624, pulse rhythm abnormalities may be detected. For example, the signal processing system may analyze the real part, imaginary part, phase, or any combination thereof of the morphology in the various regions. As another example, the signal processing system may analyze characteristics such as energy parameters in the various regions. It will be understood that any other suitable energy parameter may also be used. The signal processing system may also calculate percentage or magnitude changes in the energy parameter over time. In an embodiment, the amplitude of the ridge of the pulse band may be analyzed in place of or in addition to the energy of the pulse band.

In some embodiments, the signal processing system may detect the occurrence of a pulse rhythm abnormality using either the calculated energy parameters or the detected morphology change. For example, based at least in part on a portion of wavelet transform 624 (e.g., a portion of region 630), the signal processing system may calculate or use one or more predetermined thresholds. If the calculated energy parameter or detected artifact exceeds a threshold, the signal processing system may determine that a pulse rhythm abnormality has occurred.

In some embodiments, PPG signal 614 and scalogram 624 are used together to detect pulse rhythm abnormalities. For example, the signal processing system detects the pulse rhythm abnormality by analyzing features of both the PPG and its corresponding scalogram. As another example, the signal processing system may detect the pulse rhythm abnormality by utilizing portions of PPG signal 614 and wavelet transform 624. For instance, the signal processing system may determine when a pulse rhythm abnormality occurs in scalogram 624 (e.g., during the time period corresponding to region 640). Based at least in part on this information, the signal processing system may compare signal characteristics of PPG signal 614 in the time period before the pulse rhythm abnormality and with signal characteristics of PPG signal 614 after the pulse rhythm abnormality. Furthermore, the signal processing system may determine when the morphology change occurs in PPG signal 614. Based at least in part on this information, the signal processing system may calculate changes in the characteristics (e.g., energy parameters) of wavelet transform 624 in the time period before the morphology change and after the morphology change.

Figure 7:
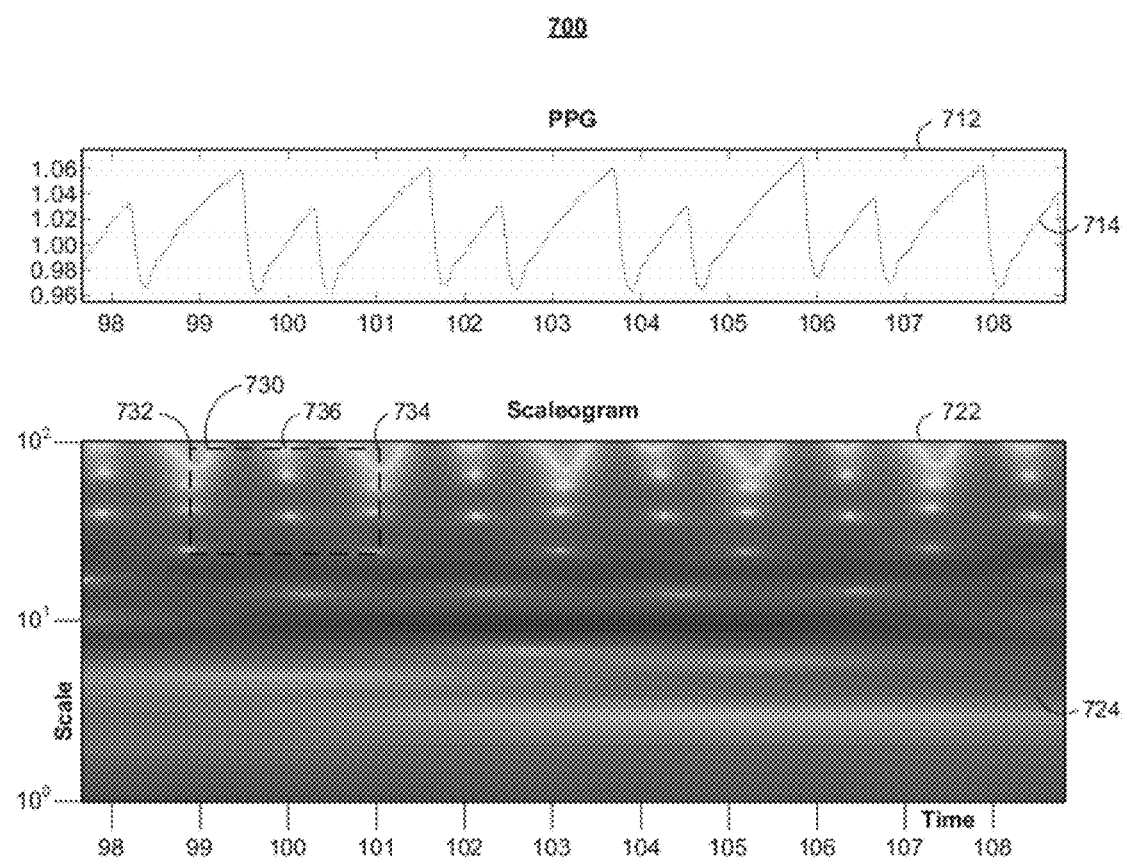
FIG. 7 shows another PPG signal and a corresponding scalogram of the PPG signal in accordance with some embodiments.

FIG. 7 illustrates a pulse rhythm abnormality in the form of a repetitive irregularity, known as bigeminy. In particular, FIG. 7 shows amplitude-time plot 712 of a PPG signal 714 and scale-time-amplitude plot 722 of scalogram 724 generated from a continuous wavelet transform of PPG signal 714. Time is represented by the horizontal axes of plots 712 and 722, amplitude is represented by the vertical axis of plot 712 and the shading of plot 722, and scale is represented by the vertical axis of plot 722.

PPG signal 714 is acquired from a patient exhibiting bigeminy. Bigeminy is characterized by an abnormal heartbeats occurring every other concurrent beat. Bigeminy can be detected in scalogram 724 because of a pattern of consecutive normal-abnormal-normal local amplitude (or, energy) minimums occurring at scales (or frequencies) greater than the pulse band, as seen for example in the pattern illustrated by consecutive points 732, 736, and 734. The signal processing system may use various metrics to detect bigeminy from PPG signal 714, scalogram 724, or both. In some embodiments, the signal processing system characterizes the amplitude, timing, period, morphology, pattern, any other suitable characteristic, or any combination thereof of a pulse or pulses of PPG signal 714, scalogram 724, or both.

In some embodiments, the signal processing system may characterize one or more of the morphology of scalogram 724, the characteristic pulse groupings of two in wavelet space (as shown in region 730, which may be progressing in time as described with reference to region 630 shown in FIG. 6), or any combination thereof. For example, the signal processing system may identify normal pulse 732 followed by abnormal pulse 736 and normal pulse 734. The signal processing system may determine that this pattern (i.e., every other pulse being abnormal) is indicative of bigeminy by calculating the amplitude values as a function of time for each scale included in region 730 and comparing the local maximum and minimum points to identify a pattern of a local minimum, as seen, for example, in the local minimum corresponding to normal pulse 734, followed by a higher amplitude local minimum such as local minimum corresponding to abnormal pulse 736.

In some embodiments, bigeminy is detected by monitoring PPG signal 714, a transformation of PPG signal 714 such as wavelet transformation 724, or both. Thus, by analyzing particular morphology changes and characteristics in various regions of scalogram 724, bigeminy may be detected. For example, the signal processing system may analyze the real part, imaginary part, phase, any other component, or any combination thereof of the morphology in the various regions, which are not shown in FIG. 7 to avoid overcomplicating the figure. As another example, the signal processing system may analyze characteristics such as energy parameters in the various regions.

Figure 8:
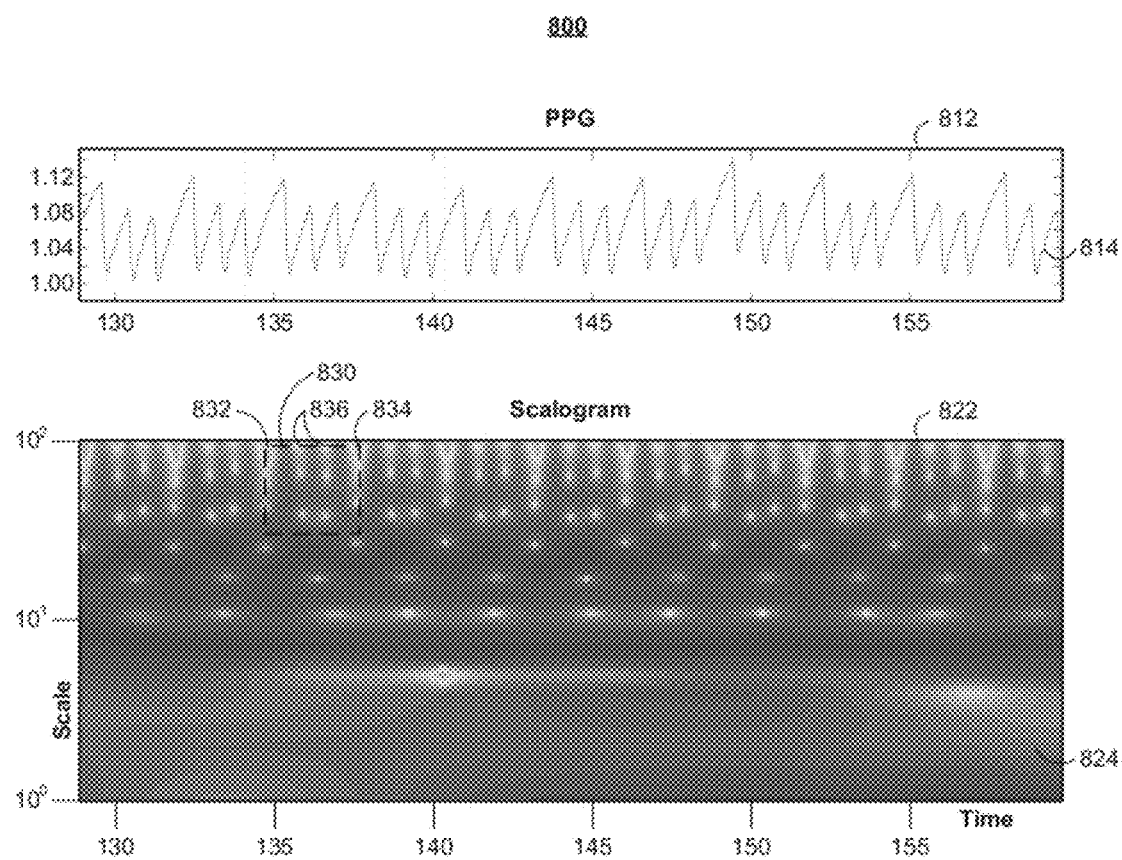
FIG. 8 shows another PPG signal and a corresponding scalogram of the PPG signal in accordance with some embodiments.

FIG. 8 illustrates a pulse rhythm abnormality in the form of a repetitive irregularity, known as trigeminy. In particular, FIG. 8 shows amplitude-time plot 812 of a PPG signal 814 and scale-time-amplitude plot 822 of scalogram 824 generated from a continuous wavelet transform of PPG signal 814. Time is represented by the horizontal axes of plots 812 and 822, amplitude is represented by the vertical axis of plot 812 and the shading of plot 822, and scale is represented by the vertical axis of plot 822.

PPG signal 814 is acquired from a patient exhibiting trigeminy. Trigeminy is characterized by abnormal heartbeats occurring at intervals of two normal beats to one abnormal heartbeat. Trigeminy can be detected in scalogram 824 because of a pattern of consecutive normal-abnormal-abnormal-normal local amplitude (or energy) minimums occurring at scales (i.e., frequencies) greater than the pulse band, as seen for example in the pattern illustrated by consecutive points 832, 836 (two in number), and 834. The signal processing system may use various metrics to detect trigeminy from PPG signal 814, scalogram 824, or both. In some embodiments, the signal processing system characterizes the amplitude, timing, period, morphology, pattern, any other suitable characteristic, or any combination thereof of a pulse or pulses of PPG signal 814, scalogram 824, or both.

In some embodiments, the signal processing system may characterize one or more of the morphology of scalogram 824, the characteristic pulse groupings of three in wavelet space (as shown in region 830, which may be progressing in time as described with reference to region 630 shown in FIG. 6), or any combination thereof. For example, the signal processing system may identify normal pulse 832 followed by abnormal pulses 836 and normal pulse 834. The signal processing system may determine that this pattern (i.e., every third pulse being abnormal) is indicative of trigeminy by calculating the amplitude values as a function of time for each scale included in region 830 and comparing the local maximum and minimum points to identify a pattern of a local minimum (e.g., local minimum corresponding to normal pulse 834) followed by two higher amplitude local minimums (e.g., local minimums corresponding to abnormal pulses 836).

In some embodiments, trigeminy is detected by monitoring PPG signal 814, a transformation of PPG signal 814 such as wavelet transformation 824, or both. Thus, by analyzing particular morphology changes and characteristics in various regions of scalogram 824, trigeminy may be detected. For example, the signal processing system may analyze the real part, imaginary part, phase, any other suitable component, or any combination thereof of the morphology in the various regions, which are not shown in FIG. 8 to avoid overcomplicating the figure. As another example, the signal processing system may analyze characteristics such as energy parameters in the various regions.

Figure 9:
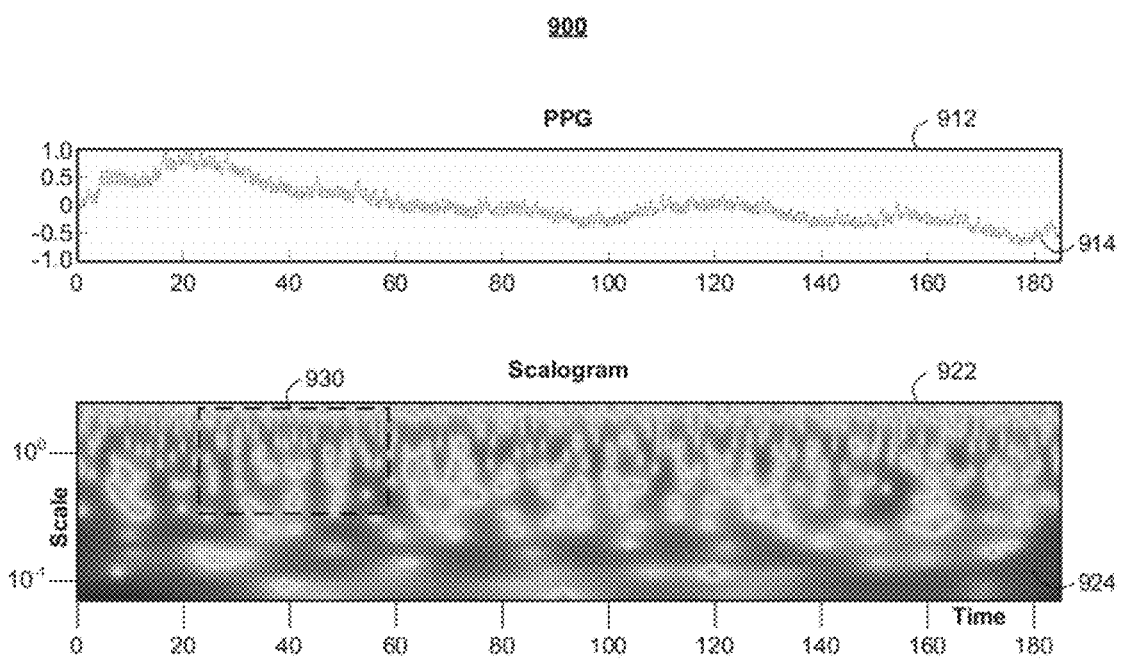
FIG. 9 shows another PPG signal and a corresponding scalogram of the PPG signal in accordance with some embodiments.

FIG. 9 illustrates a pulse rhythm abnormality indicative of extensive atrial fibrillation. As shown, the scalogram is nearly void of any regularities. In particular, FIG. 9 shows amplitude-time plot 912 of a PPG signal 914 and scale-time-amplitude plot 922 of scalogram 924 generated from a continuous wavelet transform of PPG signal 914. Time is represented by the horizontal axes of plots 912 and 922, amplitude is represented by the vertical axis of plot 912 and the shading of plot 922, and scale is represented by the vertical axis of plot 922.

PPG signal 914 is acquired from a patient exhibiting atrial fibrillation. Atrial fibrillation is characterized by erratic heart QRS intervals and manifests itself in PPG signal 914 as erratically varying amplitudes and periods of the pulses. Atrial fibrillation can be detected in scalogram 924 by the absence of a pulse band and the absence of a pattern of local minimum and maximum points at scales (i.e., frequencies) above an expected pulse band based on historical heartbeat or pulse rhythm data for a certain patient or patient type. The signal processing system may use various metrics to detect atrial fibrillation from PPG signal 914, scalogram 924, or both. In some embodiments, the signal processing system may characterize the amplitude, timing, period, morphology, or any combination thereof of a pulse, pulses, or absence thereof of PPG signal 914, scalogram 924, or both.

In some embodiments, the signal processing system may characterize the morphology, the erratic energy distribution within the vicinity of the pulse band of scalogram 924 (as shown in region 930, which may be progressing in time as described with reference to region 630 shown in FIG. 6), any other suitable characteristic, or any combination thereof. For example, the signal processing system may identify the absence of normal pulses in region 930. In another example, the signal processing system may identify the absence of a pulse band in scalogram 924, region 930, or both. The signal processing system may determine that this pattern (i.e., no normal pulse pattern) is indicative of atrial fibrillation.

In some embodiments, atrial fibrillation is detected by monitoring PPG signal 914, a transformation of PPG signal 914 such as wavelet transformation 924, or both. Thus, by analyzing particular morphology changes and characteristics in various regions of scalogram 924, atrial fibrillation may be detected. For example, the signal processing system may analyze the real part, imaginary part, phase, or any combination thereof of the morphology in the various regions. As another example, the signal processing system may analyze characteristics such as energy parameters in the various regions.

Figure 10:
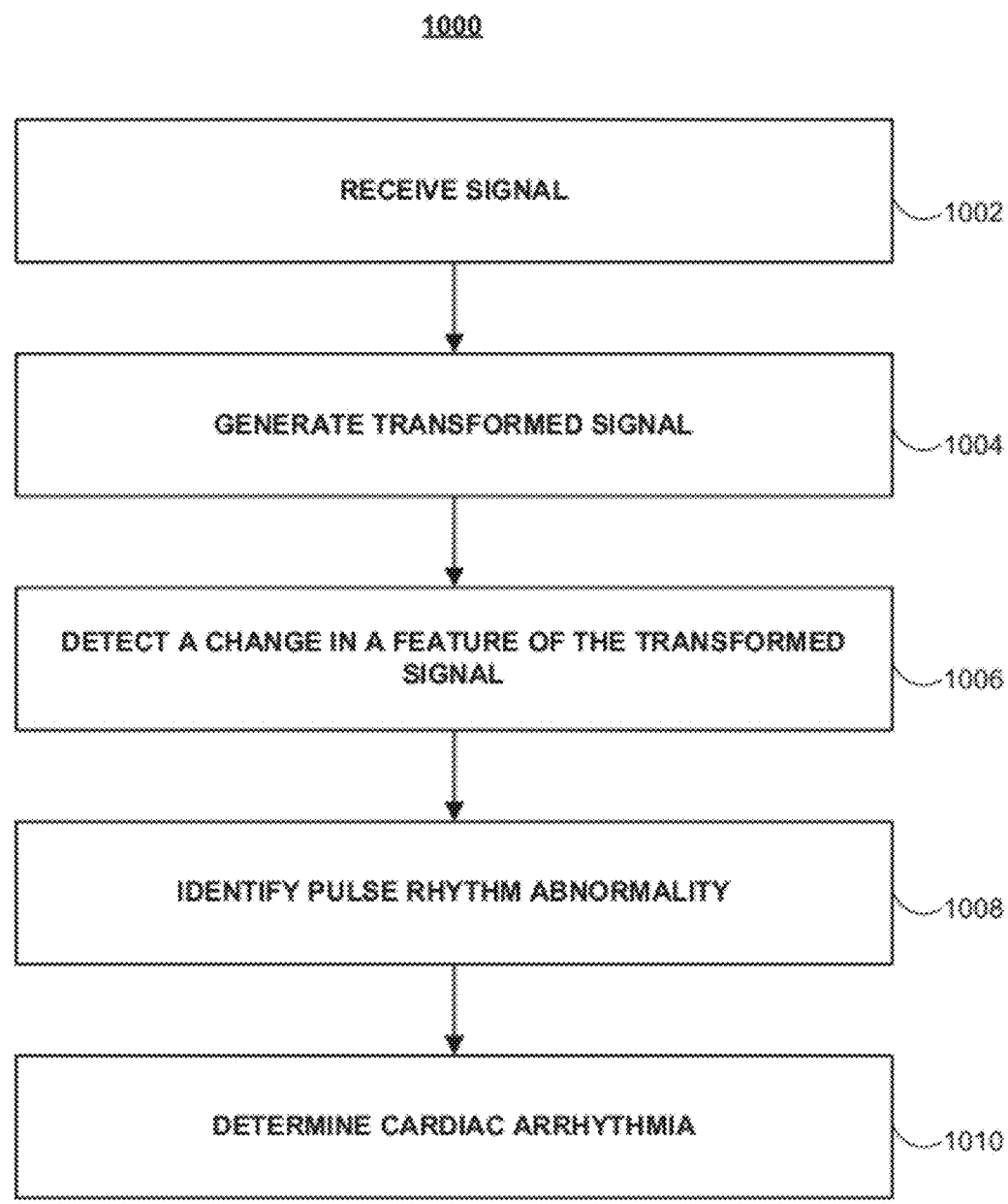
FIG. 10 is a flow chart of illustrative steps involved in determining cardiac arrhythmia in accordance with some embodiments.

FIG. 10 is a flow diagram 1000 of illustrative steps involved in determining cardiac arrhythmia based on an identified pulse rhythm abnormality in a transformation of a monitored PPG signal. The steps of flow diagram 1000 may be performed by processor 412 or may be performed by any suitable processing device communicatively coupled to monitor 14 (FIGS. 1 and 2). It will be noted that the steps of flow diagram 1400 may be performed in any suitable order, and one or more steps may be omitted entirely according to the context and application.

At step 1002, a signal (e.g., signal 416 shown in FIG. 4) is received from a patient (e.g., patient 40 of FIG. 2). The received signal may be generated by sensor unit 12 (FIGS. 1-2), which may include any of the physiological sensors described herein, or any other sensor. A received signal may be signal 416, generated by pre-processor 420 coupled between processor 412 and sensor 418 (FIG. 4). A received signal may include multiple signals, for example, in the form of a multi-dimensional vector signal or a frequency-multiplexed or time-multiplexed signal. In certain embodiments, the signal received at step 1002 includes a PPG signal, such as PPG signal 500 of FIG. 5, PPG signal 614 of FIG. 6, PPG signal 714 of FIG. 7, PPG signal 814 of FIG. 8, PPG signal 914 of FIG. 9, or any other suitable signal.

At step 1004, a transformed signal is generated from the signal received at step 1002. The processing at step 1004 may include transforming a signal into another domain, such as a Fourier, wavelet, spectral, scale, time, time-spectral, time-scale domain, or any transform space using, for example, processor 412. For example, a scalogram (e.g., scalogram 624 shown in FIG. 6, scalogram 724 shown in FIG. 7, scalogram 824 shown in FIG. 8, scalogram 924 shown in FIG. 9) may be generated by performing a wavelet transformation of a received PPG signal using a processor (e.g., processor 412 shown in FIG. 4). The wavelet transform may, for example, be a continuous or discrete wavelet transform. A transformation may include a continuous wavelet transformation as described, for example, in Paul S. Addison, The Illustrated Wavelet Transform Handbook (Taylor & Francis Group 2002).

Any of the operations described herein may be applied to a portion or portions of a received signal. An operation may be broken into one or more stages, performed by one or more devices, or both within signal processing system 400 of FIG. 4 (which may itself be a part of patient monitoring system 10 of FIGS. 1 and 2). In some embodiments, a filtering technique is applied by input signal generator 410 (FIG. 4) prior to passing the resulting input signal 416 (FIG. 4) to processor 412, where it may undergo a transformation. For example, step 1004 may include filtering a signal, such as signal 416 (FIG. 4), mathematically manipulating a signal, convolving a signal with a reference signal, or any combination thereof.

At step 1006, the signal processing system detects a change in a feature of the transformed signal. In some embodiments, the signal processing system calculates characteristics of the scalogram such as an energy parameter, morphology, pattern, or any combination thereof within a region (e.g., region 630 of FIG. 6, region 730 of FIG. 7, region 830 of FIG. 8, region 930 of FIG. 9) of the scalogram. The size and shape of the region may be selected in any suitable way. For example, the height and location of the region may be fixed or may be dynamically changed to cover a band or region of interest in the scalogram.

At step 1008, the signal processing system identifies a pulse rhythm abnormality based on the detected change in the feature of the transformed signal. For example, the signal processing system may determine that a detected pattern of normal pulses (e.g., normal pulses 632 shown in FIG. 6) followed by an abnormal pulse (e.g., abnormal pulse 646) is indicative of an occasional or isolated irregularity such as an ectopic beat. In another example, the signal processing system may determine that a detected pattern of a normal pulse (e.g., normal pulse 732 shown in FIG. 7) followed by an abnormal pulse (e.g., abnormal pulse 736) is indicative of bigeminy (i.e., every other pulse being abnormal). In another example, the signal processing system may determine that a detected pattern of a normal pulse (e.g., normal pulse 832 shown in FIG. 8) followed by two abnormal pulses (e.g., abnormal pulses 836) is indicative of trigeminy (i.e., every third pulse being abnormal). In another example, the signal processing system may determine that an absence of normal pulses (e.g., region 930 shown in FIG. 9) is indicative of atrial fibrillation.

At step 1010, the signal processing system analyzes the detected change in the feature of the transformed signal, identified pulse rhythm abnormality, or both to identify one or more irregularities in the scalogram patterns, which can be used to determine physiological information, such as cardiac arrhythmia. For example, the detection of a pulse rhythm abnormality may be used to identify or diagnose arrhythmias and heartbeat irregularities in the patient such as, for example, atrial flutter, atrial fibrillation, sinus tachycardia, ventricular tachycardia, ventricular fibrillation, bradycardia, bigeminy, trigeminy, an isolated irregularity such as an ectopic beat, any other suitable physiological information, or any combination thereof based on the pulse rhythm abnormality information.

The signal processing system may also determine cardiac arrhythmia by analyzing an original signal and the transform of that signal. For example, the signal processing system may determine when a change in a feature of the transformed signal occurs. Based at least in part on this information, the signal processing system may analyze changes in the signal characteristics of the original signal before and after the occurrence of the detected change in the transformed signal to determine whether a pulse rhythm abnormality occurs. For example, the signal characteristics of the original signal prior to the occurrence of the detected change may be compared to the signal characteristics of the original signal after the occurrence of the artifact.

In some embodiments, the detection of a pulse rhythm abnormality may also cause an action to be performed (e.g., as an optional step of flow diagram 1000). For example, processor 416 (FIG. 4) may provide a flag that indicates that further analysis needs to be performed. In another example, processor 416 may output an indication of arrhythmia or an indication of the specific arrhythmia type to display 20 (FIG. 1), display 28 (FIG. 1), any other suitable component (e.g., via output 414 shown in FIG. 4), or any combination thereof in response to the detection of a pulse rhythm abnormality. In other implementations, processor 416 may provide an audible alarm, visual alarm, any other suitable alarm, or any combination thereof to output 414, monitor 14, monitor 26, any other suitable component, or any combination thereof in response to the detection of a pulse rhythm abnormality (e.g., associated with an arrhythmia). In some embodiments, respiratory rate, pulse rate, any other suitable physiological information, or any combination thereof may be displayed (e.g., on display 20, display 28, or both shown in FIG. 1) together with the arrhythmia information. In some embodiments, arrhythmia information may replace physiological information displayed on a display screen.

It will be understood that the foregoing is only illustrative of the principles of the disclosure, and that the disclosure can be practiced by other than the described embodiments, which are presented for purposes of illustration and not of limitation. Variations and modifications will occur to those of skill in the art after reviewing this disclosure. The disclosed features may be implemented, in any combination and subcombinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

What is claimed is:

1. A method for determining cardiac arrhythmia in a patient comprising:
   electronically receiving a photoplethysmograph signal of a subject from a sensing device, wherein the photoplethysmograph signal comprises a plurality of downstroke regions;
   calculating a measure of a first downstroke region;
   calculating an average measure of two or more downstroke regions;
   comparing the measure of the first downstroke region and the average measure;
   detecting a change in a feature of the signal based at least in part on the comparison;
   generating a transformed signal based at least in part on a transformation of the photoplethysmograph signal;
   detecting a change in a feature of the transformed signal;
   identifying information indicative of a pulse rhythm abnormality based at least in part on the detected change in the feature of the transformed signal; and
   determining cardiac arrhythmia in the subject based at least in part on the information indicative of the pulse rhythm abnormality and the detected change in the feature of the photoplethysmograph signal.

2. The method of claim 1, wherein the detecting the change in the feature of the transformed signal comprises detecting a change in the feature of the transformed signal based at least in part on a comparison of the feature of the transformed signal and a threshold value.

3. The method of claim 1, wherein the cardiac arrhythmia comprises one of bigeminy, trigeminy, and a combination thereof.

4. The method of claim 1, further comprising providing for display an indication of cardiac arrhythmia based at least in part on the determined cardiac arrhythmia.

5. A system for determining physiological information about a subject, the system comprising:
   a signal input configured to receive a photoplethysmograph signal of a subject from a sensing device; and
   electronic processing equipment coupled to the signal input, the electronic processing equipment configured to:
      receive the photoplethysmograph signal;
      generate a scalogram based at least in part on a wavelet transformation of the photoplethysmograph signal, wherein the scalogram comprises a pulse band region, a region of scales greater than the pulse band region, and a region of scales lower than the pulse band region;
      determine a parameter indicative of energy distribution of the scalogram for a time interval;
      compare the parameter indicative of energy distribution of the scalogram for the time interval against a reference energy parameter value, wherein the reference energy parameter value comprises an average measure of the energy parameter indicative of distribution of the scalogram for two or more time intervals;
      detect a pattern of changes in an energy distribution of one or more of the pulse band region, the region of scales greater than the pulse band region, and the region of scales lower than the pulse band region based at least in part on the comparison;
      identify information indicative of a pulse rhythm abnormality based at least in part on the detected pattern of changes, wherein the pulse rhythm abnormality comprises a repetitive irregularity indicated by a pattern of normal and abnormal pulse characteristics; and
      determine cardiac arrhythmia in the subject based at least in part on the information indicative of the pulse rhythm abnormality.

6. The system of claim 5, wherein the photoplethysmograph signal comprises a plurality of pulse regions, and wherein the electronic processing equipment is further configured to:
   calculate a measure of the period of a first pulse region;
   calculate an average measure of the periods of two or more pulse regions;
   compare the measure of the period of the first pulse region and the average measure of the periods; and
   detect a pattern of changes in a feature of the signal based at least in part on the comparison of the measure of the period of the first pulse region and the average measure of the periods.

7. The system of claim 5, wherein the photoplethysmograph signal comprises a plurality of pulse regions, and wherein the electronic processing equipment is further configured to:
   calculate a measure of the area of a first pulse region;
   calculate an average measure of the areas of two or more pulse regions;
   compare the measure of the area of the first pulse region and the average measure of the areas; and
   detect a pattern of changes in a feature of the signal based at least in part on the comparison of the measure of the area of the first pulse region and the average measure of the areas.

8. The system of claim 5, wherein the cardiac arrhythmia comprises one of bigeminy, trigeminy, and a combination thereof.

9. The system of claim 5, wherein the electronic processing equipment is further configured to provide for display an indication of cardiac arrhythmia based at least in part on the determined cardiac arrhythmia.

10. A system for determining physiological information about a subject, the system comprising:
   a signal input configured to receive a photoplethysmograph signal of a subject from a sensing device, wherein the photoplethysmograph signal comprises a plurality of downstroke regions; and electronic processing equipment coupled to the signal input, the electronic processing equipment configured to:
receive the photoplethysmograph signal;
calculate a measure of a first downstroke region;
calculate an average measure of two or more downstroke regions;
compare the measure of the first downstroke region and the average measure;
detect a pattern of changes in a feature of the signal based at least in part on the comparison;
generate a scalogram based at least in part on a wavelet transformation of the photoplethysmograph signal, wherein the scalogram comprises a pulse band region, a region of scales greater than the pulse band region, and a region of scales lower than the pulse band region;
determine a parameter indicative of energy distribution of the scalogram for a time interval;
compare the parameter indicative of energy distribution of the scalogram for the time interval against a reference energy parameter value;
detect a pattern of changes in an energy distribution of one or more of the pulse band region, the region of scales greater than the pulse band region, and the region of scales lower than the pulse band region based at least in part on the comparison;
identify information indicative of a pulse rhythm abnormality based at least in part on the detected patterns of changes, wherein the pulse rhythm abnormality comprises a repetitive irregularity indicated by a pattern of normal and abnormal pulse characteristics; and
determine cardiac arrhythmia in the subject based at least in part on the information indicative of the pulse rhythm abnormality.

11. The system of claim 10, wherein the reference energy parameter value comprises a threshold value.

12. The system of claim 10, wherein the cardiac arrhythmia comprises one of bigeminy, trigeminy, and a combination thereof.

13. The system of claim 10, wherein the electronic processing equipment is further configured to provide for display an indication of cardiac arrhythmia based at least in part on the determined cardiac arrhythmia.

14. A non-transitory computer-readable medium for use in determining cardiac arrhythmia in a patient, the computer-readable medium having computer program instructions recorded thereon for:
electronically receiving a photoplethysmograph signal of a subject from a sensing device, wherein the photoplethysmograph signal comprises a plurality of downstroke regions;
calculating a measure of a first downstroke region;
calculating an average measure of two or more downstroke regions;
comparing the measure of the first downstroke region and the average measure;
detecting a change in a feature of the signal based at least in part on the comparison;
generating a transformed signal based at least in part on a transformation of the photoplethysmograph signal;
detecting a change in a feature of the transformed signal;
identifying information indicative of a pulse rhythm abnormality based at least in part on the detected change in the feature of the transformed signal; and
determining cardiac arrhythmia in the subject based at least in part on the information indicative of the pulse rhythm abnormality.

* * * * *